US006426082B1

(12) United States Patent
Ueda et al.

(10) Patent No.: US 6,426,082 B1
(45) Date of Patent: Jul. 30, 2002

(54) AQUEOUS SUSPENSION FORMULATION OF ENCAPSULATED PESTICIDE

(75) Inventors: Nobuhito Ueda, Ashiya; Toshiro Ohtsubo, Sanda, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/306,389

(22) Filed: May 6, 1999

(30) Foreign Application Priority Data

May 8, 1998 (JP) .............................. 10-126024

(51) Int. Cl.$^7$ ................................ A01N 25/28
(52) U.S. Cl. .................. 424/408; 424/417; 514/521; 514/531
(58) Field of Search ............... 424/408, 417; 514/521, 531

(56) References Cited

U.S. PATENT DOCUMENTS 4,534,783 A * 8/1985 Beestman ..................... 71/27
5,089,041 A * 2/1992 Thompson et al. ......... 71/64.11
5,292,533 A * 3/1994 McMahon et al. ........... 424/408
5,516,520 A   5/1996 Yang et al. .................. 424/408
5,576,008 A  11/1996 Yang et al. .................. 424/408
5,651,975 A * 7/1997 Harju-Jeanty et al. ...... 424/406
5,705,193 A * 1/1998 Bourgogne et al. ......... 424/489
5,972,363 A * 10/1999 Clikeman et al. ............ 424/408

FOREIGN PATENT DOCUMENTS

JP          07-96479       *  8/1995

* cited by examiner

*Primary Examiner*—Neil S. Levy
(74) *Attorney, Agent, or Firm*—Sughrue Mion, PLLC

(57) ABSTRACT

An aqueous suspension formulation of encapsulated pesticide comprising 3 to 30% by weight of nonionic water-soluble substance which is a solid at room temperature and has 50 to 700 of molecular weight is easy to handle, excellent in preservative stability and highly antiseptic.

6 Claims, No Drawings

AQUEOUS SUSPENSION FORMULATION OF ENCAPSULATED PESTICIDE

FIELD OF THE INVENTION

The present invention relates to an aqueous suspension formulation of encapsulated pesticide.

BACKGROUND OF THE INVENTION

Recently, aqueous suspension of encapsulated pesticide which is obtainable by microencapsulation process of a pesticidal active ingredient in water have been attracted attention in view of stabilization of active ingredient, persistency of efficacy, decrease of toxicity and so on.

It is known to add a thickner, such as polysalcharides and mineral powders, for keeping an aqueous suspension of encapsulated pesticide stable for a long period. However, the excess addition of a thickner makes the aqueous suspension sticky and it often causes the difficulty of dealing the aqueous suspension.

SUMMARY OF THE INVENTION

The object of the present invention is to serve an aqueous suspension formulation of encapsulated pesticide which is easy to handle and excellent in preservative stability.

The present invention is the aqueous suspension formulation of encapsulated pesticide containing a specific amount of a specific nonionic water-soluble substance.

In other words, the present invention relates to an aqueous suspension formulation of encapsulated pesticide comprising 3 to 30% by weight of nonionic water-soluble substance which is solid at room temperature and has 50 to 700 of molecular weight (hereinafter referred as "the present microencapsulated slurry formulation"). The present microencapsulated slurry formulation is also highly antiseptic.

DETAILED DESCRIPTION OF THE INVENTION

The water-soluble substance utilized in the present invention has 50 to 700 of molecular weight, and it is solid at room temperature and nonionic water-soluble substance. And it usually has no surfactant ability. Examples of the water-soluble substance used in the present invention include water-soluble organic compounds such as sugars (e.g. monosaccharide oligosaccharide and so on) and urea (molecular weight:60).

Examples of the monosaccharide include triose such as glyceraldehyde (m.w.:90) and dioxyacetone (m.w.:90); tetraose such as erythrose (m.w.:120), threose (m.w.:120) and erythrulose (m.w.:120); pentose such as ribose (m.w. :150), arabinose (m.w.:150), xylose (m.w.:150), lyxose (m.w.:150) and xylulose (m.w.:150); hexose such as glucose (m.w.:180), mannose (m.w.:180), galactose (m.w.:180), fructose (m.w.:180), sorbose (m.w.:180) and tagatose (m.w.:180); heptose such as mannoheptose (m.w.:210) and sedoheptulose (m.w.:210); and monosaccharide derivatives such as sorbitol (m.w.:182), mannitol (m.w.:182) and glucuronic acid (m.w.:194).

Examples of the oligosaccharide include disaccharide such as cellobiose (m.w.:342), trehalose (m.w.:342), lactose (m.w.:342) and sucrose (m.w.:342); trisaccharide such as maltotriose (m.w.:504); and tetrasaccharide such as maltotetraose (m.w.:666). The amount of the water-soluble substance used in the invention is 3 to 30% by weight, preferably 5 to 20% by weight in the present microencapsulated slurry formulation.

The present microencapsulated slurry formulation is an aqueoue suspension of microcapsules (microencapsulated pesticidal active ingredient in the wall substance) and usually comprises an encapsulated pesticidal active ingredient, the water-soluble substance used in the invention, water, a disersant and optionally additives such as a preventing agent for precipitating crystaline, a fluidity-adjusting agent and an antifreezing agent.

The average diameter of the microcapsules is usually 0.1 to 200 $\mu$m, preferably 1 to 100 $\mu$m.

The pesticidal active ingredients include insecticidal, fungicidal, herbicidal, plant growth regulating and insect growth regulating compounds and so on, and are exemplified by organophosphorus compounds such as fenitrothion [O,O-dimethyl O-(3-methyl-4-nitrophenyl) phosphorothioate], fenthion[O,O-dimethyl O-(3-methyl-4-(methylthio)phenyl)phosphorothioate], diazinon[O,O-diethyl O-2-isopropyl-6-methylpyrimidin-4-yl phosphorothioate], chlorpyrifos[O,O-diethyl O-3,5,6-trichloro-2-pyridyl phosphorothioate], acephate[O,S-dimethyl acetylphosphoramidothioate], methidathion[S-2,3-dihydro-5-methoxy-2-oxo-1,3,4-thiadiazol-3-ylmethyl O,O-dimethyl phosphorodithioate], disulfoton[O,O-diethyl S-2-ethylthioethyl phosphorodithioate], DDVP[2,2-dichlorovinyl dimethyl phosphate], sulprofos[O-ethyl O-4-(methylthio)phenyl S-propyl phosphorodithioate], cyanophos[O-4-cyanophenyl O,O-dimethyl phosphorothioate], dioxabenzofos[2-methoxy-4H-1,3,2-benzodioxaphosphorine 2-sulfide], dimethoate[O,O-dimethyl S-(N-methylcarbamoylmethyl) dithiophosphate], phenthoate[ethyl 2-dimethoxyphosphinothioylthio(phenyl) acetate], malathion[diethyl (dimethoxyphosphinothioylthio) succinate], trichlorfon[dimethyl 2,2,2-trichloro-1-hydroxyethylphosphonate], azinphos-methyl[S-3,4-dihydro-4-oxo-1,2,3-benzotriazin-3-ylmethyl O,O-dimethyl phosphorodithioate], monocrotophos[dimethyl {(E)-1-methyl-2-(methylcarbamoyl)vinyl}phosphate], ethion[O,O, O',O'-tetraethyl-S,S'-methylenebis(phosphorodithioate)] and so on; carbamate compounds such as BPMC [2-sec-butylphenyl methylcarbamate], benfuracarb[ethyl N-{2,3-dihydro-2,2-dimethylbenzofuran-7-yloxycarbonyl(methyl) aminothio}-N-isopropyl-β-alaninate], propoxur[2-isopropoxyphenyl N-methylcarbamate], carbosulfan[2,3-dihydro-2,2-dimethyl-7-benzo[b]furanyl N-dibutylamninothio-N-methylcarbamate], carbaryl[1-naphthyl N-methylcarbamate], methomyl[S-methyl N-(methylcarbamoyloxy) thioacetimidate], ethiofencarb[2-(ethylthiomethyl)phenyl methylcarbamate], aldicarb [2-methyl-2-(methylthio)propionaldehyde O-methylcarbamoyloxime], oxamyl[N,N-dimnethyl-2-methylcarbamoyloxyimino-2-(methylthio)acetamide], fenothiocarb[S-4-phenoxybutyl N,N-dimethylthiocarbamate], and so on; pyrethroid compounds such as etofenprox[2-(4-ethoxyphenyl)-2-methyl-1-(3-phenoxybenzyl)oxypropane], fenvalerate[(RS)-α-cyano-3-phenoxybenzyl (RS)-2-(4-chlorophenyl)-3-methylbutyrate], esfenvalerate[(S)-α-cyano-3-phenoxybenzyl (S)-2-(4-chlorophenyl)-3-methylbutyrate], fenpropathrin[(RS)-α-cyano-3-phenoxybenzyl 2,2,3,3-tetramethylcyclopropanecarboxylate], cypermethrin[(RS)-α-cyano-3-phenoxybenzyl (1RS)-cis,trans-3-(2,2-dichlorovinyl)-2,2-dimethylcyclopropanecarboxylate], permethrin[3-phenoxybenzyl (1RS)-cis,trans-3-(2,2-dichlorovinyl)-2,2-dimethylcyclopropanecarboxylate], cyhalothrin[(RS)-α-cyano-3-phenoxybenzyl (1RS,3Z)-cis- 3-(2-chloro-3,3,3-trifluoroprop-1-enyl)-2,2-dimethylcyclopropanecarboxylate], deltamethrin[(S)-α-cyano-3-phenoxybenzyl (1R)-cis-3-(2,2-dibromovinyl)-2,2-dimethylcyclopropanecarboxylate], cyloprothrin[(RS)-α-cyano-3-phenoxybenzyl (RS)-2,2-dichloro-1-(4-ethoxyphenyl) cyclopropanecarboxylate], fluvalinate[α-cyano-3-phenoxybenzyl N-(2-chloro-α, α, α-trifluoro-p-tolyl)-D-valinate], bifenthrin[2-methyl-3-phenylbenzyl (1RS,3Z)-cis-3-(2-chloro-3,3,3-trifluoro-1-propenyl)-2,2-dimethylcyclopropanecarboxylate], halfenprox[2-(4-bromodifluoromethoxyphenyl)-2-methyl-1-(3-phenoxybenzyl) methylpropane], tralomethrin[(S)-α-cyano-3-phenoxybenzyl (1R)-cis-3-(1,2,2,2-tetrabromoethyl)-2,2-dimethylcyclopropanecarboxylate], silafluofen[(4-ethoxyphenyl)-{3-(4-fluoro-3-phenoxyphenyl) propyl}dimethylsilane], d-phenothrin[3-phenoxybenzyl (1R)-cis,trans-2,2-dimethyl-3-(2-methyl-1-propenyl) cyclopropanecarboxylate], cyphenothrin[(RS)-α-cyano-3-phenoxybenzyl (1R)-cis,trans-2,2-dimethyl-3-(2-methyl-1-propenyl)cyclopropanecarboxylate], d-resmethrin[5-benzyl-3-furylmethyl (1R)-cis,trans-2,2-dimethyl-3-(2-methyl-1-propenyl)cyclopropanecarboxylate], acrinathrin[(S)-α-cyano-3-phenoxybenzyl (1R,3Z)-cis-(2,2-dimethyl-3-{3-oxo-3-(1,1,1,3,3,3-hexafluoropropyloxy) propenyl}cyclopropanecarboxylate], cyfluthrin [(RS)-α-cyano-4-fluoro-3-phenoxybenzyl 3-(2,2-dichlorovinyl)-2,2-dimethylcyclopropanecarboxylate], tefluthrin[2,3,5,6-tetrafluoro-4-methylbenzyl (1RS,3Z)-cis-3-(2-chloro-3,3,3-trifluoro-1-propenyl)-2,2-dimethylcyclopropanecarboxylate], transfluthrin[2,3,5,6-tetrafluorobenzyl (1R)-trans-3-(2,2-dichlorovinyl)-2,2-dimethylcyclopropanecarboxylate], tetramethrin[3,4,5,6-tetrahydrophthalimidomethyl (1RS)-cis,trans-2,2-dimethyl-3-(2-methyl-1-propenyl) cyclopropanecarboxylate], allethrin[(RS)-2-methyl-4-oxo-3-(2-propenyl)-2-cyclopenten-1-yl (1RS)-cis,trans-2,2-dimethyl-3-(2-methyl-1-propenyl) cyclopropanecarboxylate], prallethrin[(S)-2-methyl-4-oxo-3-(2-propynyl)-2-cyclopenten-1-yl (1R)-cis,trans-2,2-dimethyl-3-(2-methyl-1-propenyl) cyclopropanecarboxylate], empenthrin[(RS)-1-ethynyl-2-methyl-2-pentenyl (1R)-cis,trans-2,2-dimethyl-3-(2-methyl-1-propenyl)cyclopropanecarboxylate], imiprothrin [2,5-dioxo-3-(2-propynyl)imidazolidin-1-ylmethyl (1R)-cis,trans-2,2-dimethyl-3-(2-methyl-1-propenyl) cyclopropanecarboxylate], d-furamethrin[5-(2-propynyl) furfuryl (1R)-cis,trans-2,2-dimethyl-3-(2-methyl-1-propenyl)cyclopropanecarboxylate], 5-(2-propynyl) furfuryl2,2,3,3-teramethylcyclopropanecarboxylate and so on; thiadiazine derivatives such as buprofezin[2-tert-butylimino-3-isopropyl-5-phenyl-1,3,5-thiadiazin-4-one] and so on; nitroimidazolidine derivatives such as imidacloprid[1-(6-chloro-3-pyridylmethyl)-N-nitroimidazolidin-2-ylideneamine] and so on; nereistoxin derivatives such as cartap[S,S'-(2-dimethylaminotrimethylene)bis(thiocarbamate)], thiocyclam[N,N-dimethyl-1,2,3-trithian-5-ylamine], bensultap[S,S'-2-dimethylaminotrimethylenedi (benzenethiosulfonate)] and so on; N-cyanoamidine derivatives such as N-cyano-N'-methyl-N'-(6-chloro-3-pyridylmethyl)acetamidine and so on; chlorinated hydrocarbon compounds such as endosulfan[6,7,8,9,10,10-hexachloro-1,5,5a,6,9,9a-hexahydro-6,9-methano-2,4,3-benzodioxathiepine oxide], γ-BHC[1,2,3,4,5,6-hexachlorocyclohexane], dicofol[1,1-bis(4-chlorophenyl)-2,2,2-trichloroethanol]; benzoylurea compounds such as chlorfluazuron[1-{3,5-dichloro-4-(3-chloro-5-trifluromethylpyridin-2-yloxy)phenyl}-3-(2,6-difluorobenzoyl)urea], teflubenzuron[1-(3,5-dichloro-2,4-difluorophenyl)-3-(2,6-difluorobenzoyl)urea], flufenoxuron [1-{4-(2-chloro-4-trifluromethylphenoxy)-2-fluorophenyl}-3-(2,6-difluorobenzoyl)urea] and so on; formarnidine derivatives such as amitraz[N,N'-{(methylimino) dimethylidine}-di-2,4-xylidine], chlordimeform[N'-(4-chloro-2-methylphenyl)-N,N-dimethylmethinimidamide] and so on; thiourea derivatives such as diafenthiuron[N-(2, 6-diisopropyl-4-phenoxyphenyl)-N'-t-butylcarbodiimide] and so on; N-phenylpyrazole compounds; metoxadiazone [5-methoxy-3-(2-methoxyphenyl)- 1,3,4-oxadiazol-2-(3H)-one]; bromopropylate[isopropyl4,4'-dibromobenzilate]; tetradifon[4-chlorophenyl2,4,5-trichlorophenyl sulfone]; chinomethionat[S,S-6-methylquinoxaline-2,3-diyl dithiocarbonate]; propargite[2-(4-tert-butylphenoxy) cyclohexylprop-2-yl sulfite]; fenbutatin oxide[bis{tris(2-methyl-2-phenylpropyl)tin}oxide]; hexythiazox[(4RS, 5RS)-5-(4-chlorophenyl)-N-chlorohexyl-4-methyl-2-oxo-1, 3-thiazolidine-3-carboxamide]; clofentezine[3,6-bis(2-chlorophenyl)-1,2,4,5-tetrazine]; pyridaben[2-tert-butyl-5-(4-tert-butylbenzylthio)-4-chloropyridazin-3(2H)-one]; fenpyroximate[tert-butyl(E)-4-[(1,3-dimethyl-5-phenoxypyrazol-4-yl)methyleneaminooxymethyl] benzoate]; tebufenpyrad[N-(4-tert-butylbenzyl)-4-chloro-3-ethyl-1-methyl-5-pyrazolecarboxamide]; polynactin complex[tetranactin, dinactin, trinactin]; pyrimidifen[5-chloro-N-[2-{4-(2-ethoxyethyl)-2,3-dimethylphenoxy}ethyl]-6-ethylpyrimidin-4-amine]; milbemectin; abamectin; avermectin; azadirachtin[AZAD]; 5-methyl[1,2,4]triazolo[3,4-b]benzothiazole; methyl1-(butylcarbamoyl)benzimidazole-2-carbamate, 6-(3,5-dichloro-4-methylphenyl)-3(2H)-pyridazine; 1-(4-chlorophenoxy)-3,3-dimethyl-1-(1H-1,2,4-triazol-1-yl) butanone; (E)-4-chloro-2-(trifluoromethyl)-N-[1-(imidazol-1-yl)-2-propoxyethylidene]aniline; 1-[N-propyl-N-[2-(2,4, 6-trichlorophenoxy)ethyl]carbamoyl]imidazole; (E)-1-(4-chlorophenyl)-4,4-dimethyl-2-(1H-1,2,4-triazol-1-yl)-1-penten-3-ol; 1-(4-chlorophenyl)-4,4-dimethyl-2-(1H-1,2,4-triazol-1-yl)pentan-3-ol; (E)-1-(2,4-dichlorophenyl)-4,4-dimethyl-2-(1H-1,2,4-triazol-1-yl)-1-penten-3-ol; 1-(2,4-dichlorophenyl)-4,4-dimethyl-2-(1H-1,2,4-triazol-1-yl) pentan-3-ol; 4-[3-(4-tert-butylphenyl)-2-methylpropyl]-2,6-dimethylmorphorine; 2-(2,4-dichlorophenyl)-1-(1H-1,2,4-triazol-1-yl)hexan-2-ol; O,O-diethyl O-2-quinoxalinyl phosphorothioate; O-(6-ethoxy-2-ethyl-4-pyrimidinyl) O,O-dimethyl phosphorothioate; 2-diethylamino-5,6-dimethylpyrimidin-4-yl dimethylcarbamate; 4-(2,4-dichlorobenzoyl)-1,3-dimethyl-5-pyrazolyl p-toluenesulfonate; 4-amino-6-( 1,1-dimethyethyl)-3-methylthio-1,2,4-triazin-5(4H)-one; 2-chloro-N-[(4-methoxy-6-methyl-1,3,5-triazin-2-yl)aminocarbonyl] benzenesulfonamide; 2-methoxycarbonyl-N-[(4,6-dimethoxypyrimidin-2-yl)aminocarbonyl] benzenesulfonamide; 2-methoxyearbonyl-N-[(4,6-dimethylpyrimidin-2-yl)aminocarbonyl] benzenesulfonamide; 2-methoxycarbonyl-N-[(4-methoxy-6-methyl-1,3,5-triazin-2-yl)aminocarbonyl] benzenesulfonamide; 2-ethoxycarbonyl-N-[(4-chloro-6-methoxypyrimidin-2-yl)aminocarbonyl] benzenesulfonamide; 2-(2-chloroethoxy)-N-[(4-methoxy-6-methyl-1,3,5-triazin-2-yl)aminocarbonyl] benzenesulfonamide; 2-methoxycarbonyl-N-[(4,6-dimethoxypyrimidin-2-yl)aminocarbonyl] phenylmethanesulfonamide; 2-methoxycarbonyl-N-[(4-methoxy-6-methyl-1,3,5-triazin-2-yl)aminocarbonyl] thiophene-3-sulfonamide; 4-ethoxycarbonyl-N-[(4,6-dimnethoxypyrimidin-2-yl)aminocarbonyl]-1- methylpyrazole-5-sulfonamide; 2-[4,5-dihydro-4-methyl-4-(1-methylethyl)-5-oxo-1H-imidazol-2-yl]-3-quinolinecarboxylic acid; 2-[4,5-dihydro-4-methyl4-(1-methylethyl)-5-oxo-1H-imidazol-2-yl]-5-ethyl-3-pyridinecarboxylic acid; methyl -6-(4-isopropyl-4-methyl-5-oxoimidazolin-2-yl)-m-toluate; methyl2-(4-isopropyl-4-methyl-5-oxoimidazolin-2-yl)-p-toluate; 2-(4-isopropyl-4-methyl-5-oxoimidazolin-2-yl)nicotinic acid; and N-(4-chlorophenyl)methyl-N-cyclopentyl-N'-phenylurea.

The content of the pesticidal active ingredient in the present microencapsulated slurry formulation is usually 1 to 50% by weight, preferably 5 to 35% by weight. And the content of the wall substance to form the microcapsules is usually 0.01 to 15% by weight, preferably 0.1 to 5% by weight based on the weight of the present microencapsulated slurry formulation. Further, the content of water is usually 30 to 90% by weight based on the weight of the present microencapsulated slurry formulation.

Examples of the microencapsulation method include interfacial polymerization method wherein microcapsule is prepared by allowing monomers, dissolved in two solvents which cannot be mixed each other, to react at the interface of the solvents (interfacial polymerization reaction) for affording polymer; in-situ method wherein microcapsule is prepared by allowing monomer, dissolved in one of two solvents which cannot be mixed each other, to react at the interface of the solvents for forming uniform wall on the surface of the core substance; phase separation method (coacervation method) that is utilized a phenomenon (coacervation) separating a thicker phase with a thinner phase by a slight change of solvent components of polymer solution wherein microcapsule wall is prepared by separating one or more colloidal polymer out at the interface by addition of a phase-separation inducing agent that has a high affinity with solvent, joint electrostatic action or hydrogen bonding; and solvent evaporation method wherein core liquid or core solid is dispersed in a solvent dissolving polymer that can form a wall material, the dispersion is further dispersed in a solvent that cannot be mixed with the above solvent, and then the above solvent is gradually evaporated to deposit polymer at the interface of the core substance.

Examples of the wall substance to form microcapsules include polyurea, polyurethane, polyamide, urea-formalin resin, melamin-formalin resin, gelatin, albumin and chitosan.

The above microencapsulation methods and the sort of the wall substances are suitably set for the objects.

The average wall thickness of the microcapsules is usually 0.001 to 10 μm, preferably 0.01 to 5 μm.

The method for adding the water-soluble substance used in the invention is not limited. It may be added to slurry of the microencapsulated pesticidal active ingredient or it may be added prior to microencapsulation. But it is preferable to add the water-soluble substance used in the invention to the slurry of the microencapsulated pesticidal active ingredient.

Examples of the dispersant include natural polysaccharides such as gum arabic; water-soluble polymer such as polyvinyl alcohol; and surfactants such as nonionic surfactants, anionic surfactants, cationic surfactants and zwitter-ionic surfactants. The content of the dispersant in the formulation of the present invention is usually 0.1 to 10% by weight, preferably 1 to 5% by weight. The dispersant is usually added prior to microencapsulation.

Examples of the preventing agent for precipitating crystalline include aromatic hydrocarbons such as phenyixylylethane, methylnaphthalene and alkylbenzene; aliphatic hydrocarbons such as hexane, octane and decane; ketones such as isophorone and cyclohexanone; esters such as dialkyl adipate (e.g. diisodecyl adipate, diisobutyl adipate) and dialkyl phthalate (e.g. ditridecyl phthalate); and N-alkylpyrrolidone such as N-methylpyrrolidone. The content of the preventing agent for precipitating crystalline is usually 1 to 40% by weight, preferably 10 to 30% by weight. The preventing agent for precipitating crystalline is usually added prior to microencapsulation.

Examples of the fluidity-adjusting agents include natural polysaccharides such as xanthan gum, rhamsan gum, locust-bean gum, carageenan and welan gum; synthetic polymers such as sodium polyacrylate; semi-synthetic polymers such as carboxymethylcellulose; mineral powders such as alminium silicate, smectite, bentonite, heclite and dry process silica; alumina sol; and so on. The content of the fluidity-adjusting agents is usually 0.01 to 5% by weight, preferably 0.05 to 1% by weight. The fluidity-adjusting agents is usually added to slurry of the microencapsulated pesticidal active ingredient.

The formulation of the present invention may optionally comprises the other auxiliaries for formulation. Examples of the auxiliaries include antifreezing agents. The typical example of the antifreezing agents is alcohols such as propylene glycol.

The present microencapsulated slurry formulation can be applied by usual method depending on the pesticidal active ingredient in the same situation that ordinary aqueous micro-suspension formulation is applied. For example, it may be applied by itself or as a water dilution for pest-controlling in paddy or field, weed-controlling in paddy or field, termite-controlling in house and cockroach-controlling indoors. As the formulation of the present invention has a low viscosity, the formulation is easily taken out a container. Therefore, it is especially useful in case that it is desired to apply a large amount of pesticide in a short tine, such as aerial application use, termite-controlling use in house and cockroach-controlling use indoors.

When it is utilized in aerial application, 0.8 to 40 liters of the present microencapsulated slurry formulation or its dilution can be usually applied per 1 hectare. One to 5 liters is standardly applied for soil-treatment of termite-controlling in house, 50 to 400 mrliliters is standardly applied for wood-treatment of termite-controlling in house and 10 to 100 mililiters is standardly applied for cockroach-controlling indoors per 1 $m^2$. The concentracion of the formulation of the present invention can be suitably set according to the desired dosage of the utilized pesticidal active ingredient.

EXAMPLES

Example 1

One hundred grams of esfenvalerate (pesticidal active ingredient), 2.1 g of Sumidur L-75 (polyisocyanate produced by Sumitomo-Bayer Urethane) and 200 g of Solvesso 200 (aromatic solvent produced by Exxon Chemical) were homogeneously mixed and added to 291.7 g of 6% by weight of aqueous solution of gum arabic containing 4 g of ethylene glycol. The mixture was stirred at 6300 rpm by T.K. Autohomomixer (homogenizer produced by Tokushukika Kogyo) and dispersed at room temperature for 5 minutes, and then stirred slowly at 60° C. for 24 hours to afford a slurry having esfenvalerate microencapsulated in polyurethane wall. To the obtained slurry, 406.2 g of aqueous solution containing 80 g of glucose, 0.5 g of xanthan gum, 1 g of aluminium silicate, 50 g of propylene glycol and 2 g of Proxel GXL (preservative produced by Zeneca) were added to afford an aqueous capsule suspension formulation having a viscosity of 240 mPa·sec containing 10% by weight of esfenvalerate.

Example 2

The same procedure as example 1 except using 70 g of sucrose in place of 80 g of glucose, 1 g of xanthan gum in place of 0.5 g and 2 g of aluminium silicate in place of 1 g gave an aqueous capsule suspension formulation having a viscosity of 910 mPa·sec containing 10% by weight of esfenvalerate.

Example 3

The same procedure as example 1 except using 96 g of urea in place of 80 g of glucose, 1 g of xanthan gum in place of 0.5 g and 2 g of aluminium silicate in place of 1 g gave an aqueous capsule suspension formulation having a viscosity of 800 mPa·sec containing 10% by weight of esfenvalerate.

Example 4

One hundred grams of esfenvalerate, 2.1 g of Sumidur L-75 and 200 g of Solvesso 200 were homogeneously mixed and added to 291.7 g of 6% by weight of aqueous solution of gum arabic containing 4 g of ethylene glycol. The mixture was stirred at 6300 rpm by T.K Autohomomixer and dispersed at room temperature for 5 minutes, and then stirred slowly at 60° C. for 24 hours to afford a slurry having esfenvalerate microencapsulated in polyurethane wall. To the obtained slurry, 406.2 g of aqueous solution containing 67.5 g of glucose, 1.05 g of xanthan gum, 50 g of propylene glycol, 2 g of Proxel GXL and 1 g of Legend MK (preservative produced by Rohm and Haas) were added to afford an aqueous capsule suspension formulation having a viscosity of 500 mPa·sec containing 10% by weight of esfenvalerate.

Example 5

One hundred grams of esfenvalerate, 2.1 g of Sumidur L-75 and 200 g of Solvesso 200 were homogeneously mixed and added to 291.7 g of 6% by weight of aqueous solution of gum arabic containing 4 g of ethylene glycol. The mixture was stirred at 6900 rpm by T.K. Autohomomixer and dispersed at room temperature for 5 minutes, and then stirred slowly at 60° C. for 24 hours to afford a slurry having esfenvalerate microencapsulated in polyurethane wall. To the obtained slurry, 406.2 g of aqueous solution containing 67.5 g of glucose, 1 g of xanthan gum, 2 g of aluminium silicate and 50 g of propylene glycol were added to afford an aqueous capsule suspension formulation containing 10% by weight of esfenvalerate.

Reference Example 1

One hundred grams of esfenvalerate, 0.5 g of Sumidur L-75 (polyisocyanate produced by Sumitomo-Bayer Urethane) and 200 g of Solvesso 200 were homogeneously mixed and added to 291.7 g of 6% by weight of aqueous solution of gum arabic containing 4 g of ethylene glycol. The mixture was stirred at 6300 rpm by T.K. Autohomomixer and dispersed at room temperature for 5 minutes, and then stirred slowly at 60° C. for 24 hours to afford a slurry having esfenvalerate microencapsulated in polyurethane wall. To the obtained slurry, 406.2 g of aqueous solution containing 2 g of xanthan gum, 4 g of aluminium silicate, 50 g of propylene glycol and 2 g of Proxel GXL were added to afford an aqueous capsule suspension formulation having a viscosity of 3800 mPa·sec containing 10% by weight of esfenvalerate.

Reference Example 2

One hundred grams of esfenvalerate, 0.5 g of Sumidur L-75 (polyisocyanate produced by Sumitomo-Bayer Urethane) and 200 g of Solvesso 200 were homogeneously mixed and added to 291.7 g of 6% by weight of aqueous solution of gum arabic containing 4 g of ethylene glycol. The mixture was stirred at 6300 rpm by T.K. Autohomomixer and dispersed at room temperature for 5 minutes, and then stirred slowly at 60° C. for 24 hours to afford a slurry having esfenvalerate microencapsulated in polyurethane wall. To the obtained slurry, 406.2 g of aqueous solution containing 1.4 g of xanthan gum, 50 g of propylene glycol, 2 g of Proxel GXL and 1 g of Legend MK were added to afford an aqueous capsule suspension formulation having a viscosity of 1000 mPa·sec containing 10% by weight of esfenvalerate.

Reference Example 3

One hundred grams of esfenvalerate, 2.1 g of Sumidur L-75 and 200 g of Solvesso 200 were homogeneously mixed and added to 291.7 g of 6% by weight of aqueous solution of gum arabic containing 4 g of ethylene glycol. The mixture was stirred at 6900 rpm by T.K. Autohomomixer and dispersed at room temperature for 5 minutes, and then stirred slowly at 60° C. for 24 hours to afford a slurry having esfenvalerate microencapsulated in polyurethane wall. To the obtained slurry, 406.2 g of aqueous solution containing 1 g of xanthan gum, 2 g of aluminium silicate and 50 g of propylene glycol were added to afford an aqueous capsule suspension formulation containing 10% by weight of esfenvalerate.

Test Example 1

One hundred grams of each aqueous capsule suspension formulation obtained in examples 1 to 4 and reference examples 1 to 2 was charged into 100 ml plastic bottle and each height ($T_1$) from the bottom of the plastic bottle to the liquid surface was measured. After each bottle containing the formulation was kept 40° C. for 3 months, the height ($T_2$) of the top clear part separated from the formulation was measured and the separation ratio was calculated by the formula below. The results are shown in table 1.

$$\text{Separation ratio}(\%) = (T_2/T_1) \times 100$$

TABLE 1

| Experimental No. | viscosity of formulation (mPa · sec) | Separation ratio (%) |
| --- | --- | --- |
| Example 1 | 240 | 0 |
| Example 2 | 910 | 0 |
| Example 3 | 800 | 0 |
| Example 4 | 500 | 0 |
| Reference example 1 | 3810 | 4 |
| Reference example 2 | 1000 | 19 |

As shown in table 1, the formulations of the present invention have a low viscosity, and so they are easy to handle. Furthermore, they are excellent in preservative stability as the separation of the formulation was not observed.

Test Example 2

Tested bacteria (*Escherichia coli*) was pre-cultivated at LB culture medium at about 26° C. for 1 day and the tested formulation (5 g) was inoculated with the pre-cultivated liquid at the concentration of 105 bacteria per ml. The bacteria was cultivated at room temperature (about 26° C.). Four days after the inoculation, the cultivated sample was streaked with platinum wire loop on the Nutrient Agar (DIFCO) plane culture medium and cultivated at room temperature. After 3 days, the generation of bacteria was observed. The results are shown in table 2.

TABLE 2

| Experimental No. | Generation of bacteria |
|---|---|
| Example 5 | ± |
| Reference example 1 | +++ |

−: observed no generation of bacteria
±: observed slight generation of bacteria
+++: observed large multiplication of bacteria

Test Example 3

The capsule suspension formulation obtained in example 5 is kept 40° C. for 1 month in a plastic bottle and then the generation of microbials is not observed.

As shown in test examples 2 and 3, the present microencapsulated slurry formulation is also antiseptic.

What is claimed is:

1. An aqueous suspension formulation of microencapsulated esfenvalerate pesticide comprising, based on the weight of the aqueous suspension formulation, 1 to 50% by weight of microencapsulated pesticide, 3 to 30% by weight of a nonionic water-soluble substance which is a solid at room temperature and has a molecular weight of 50 to 700, and water.

2. The formulation according to claim 1, wherein the formulation further contains 0.1 to 10% by weight of a dispersant.

3. The formulation according to claim 1, wherein the nonionic water-soluble substance is urea.

4. The formulation according to claim 1, wherein the nonionic water-soluble substance is a sugar.

5. The formulation according to claim 4, wherein the sugar is a monosaccharide or oligosaccharide.

6. A method for stabilizing an aqueous suspension micfoencapsulated formulation of esfenvalerate pesticide which comprises adding a nonionic water-soluble substance which is a solid at room temperature and has a molecular weight of 50 to 700 to the aqueous suspension to make the content of the nonionic water-soluble substance 3 to 30% by weight, based on the weight of the aqueous suspension formulation.

* * * * *